United States Patent
McDonald et al.

(10) Patent No.: US 9,572,967 B2
(45) Date of Patent: Feb. 21, 2017

(54) ANTISEPTIC APPLICATOR

(71) Applicant: CAREFUSION 2200, INC., San Diego, CA (US)

(72) Inventors: James Patrick McDonald, El Paso, TX (US); Manuel Guzman, El Paso, TX (US)

(73) Assignee: Carefusion 2200, Inc., San Diego, CA (US)

( * ) Notice: Subject to any disclaimer, the term of this patent is extended or adjusted under 35 U.S.C. 154(b) by 312 days.

(21) Appl. No.: 14/201,508

(22) Filed: Mar. 7, 2014

(65) Prior Publication Data

US 2014/0186092 A1    Jul. 3, 2014

Related U.S. Application Data (63) Continuation of application No. 12/826,139, filed on Jun. 29, 2010, now Pat. No. 8,708,983.

(51) Int. Cl.
    *A61M 35/00*      (2006.01)

(52) U.S. Cl.
    CPC ................... *A61M 35/003* (2013.01)

(58) Field of Classification Search
    CPC ............ A61M 35/003; A61M 35/00
    USPC ................... 604/310; 401/203–205
    See application file for complete search history.

(56) References Cited

U.S. PATENT DOCUMENTS

| | | |
|---|---|---|
| 3,261,515 A | 7/1966 | Luedtke |
| 3,757,782 A | 9/1973 | Aiken |
| 4,415,288 A | 11/1983 | Gordon et al. |
| 4,498,796 A | 2/1985 | Gordon et al. |
| 4,878,774 A | 11/1989 | Karasin et al. |
| 5,288,159 A | 2/1994 | Wirt |
| 5,308,180 A | 5/1994 | Pournoor et al. |
| 5,435,660 A | 7/1995 | Wirt |
| 5,445,462 A | 8/1995 | Johnson et al. |
| 5,658,084 A | 8/1997 | Wirt |
| 5,769,552 A | 6/1998 | Kelley |
| 5,772,346 A | 6/1998 | Edwards |
| 5,791,801 A | 8/1998 | Miller |
| 5,927,884 A | 7/1999 | Kao |
| 6,371,675 B1 | 4/2002 | Hoang et al. |
| 6,488,665 B1 | 12/2002 | Severin et al. |
| 6,533,484 B1 | 3/2003 | Osei et al. |
| 6,536,617 B2 | 3/2003 | White et al. |
| 6,673,303 B2 | 1/2004 | White et al. |
| 6,916,133 B2 | 7/2005 | Hoang et al. |
| 7,201,525 B2 | 4/2007 | Mohiuddin |
| 7,594,775 B1 * | 9/2009 | Yoo ............ A45D 34/042 401/202 |
| 8,123,426 B2 * | 2/2012 | Byun ........... B65D 35/36 401/202 |
| 2003/0075200 A1 * | 4/2003 | Gueret ............ A45D 34/04 132/320 |
| 2004/0262337 A1 | 12/2004 | Young |

(Continued)

*Primary Examiner* — Susan Su
(74) *Attorney, Agent, or Firm* — Arent Fox LLP (57) ABSTRACT

An applicator assembly includes a body having a proximal and a distal end, a container slidably coupled to the body, a valve cap coupled to the container, and an application member attached to the distal end, wherein an interior of the container is placed in fluid communication with the application member by way of a fluid conduit that is only accessible when one of the body and the container are axially translated in an opposite direction away from each other.

20 Claims, 6 Drawing Sheets

(56) References Cited

U.S. PATENT DOCUMENTS

| | | |
|---|---|---|
| 2006/0039742 A1 | 2/2006 | Cable, Jr. et al. |
| 2006/0062629 A1 | 3/2006 | Colburn et al. |
| 2006/0285913 A1* | 12/2006 | Koptis .................. A45D 40/26 401/205 |
| 2009/0032533 A1 | 2/2009 | Kessell et al. |
| 2011/0082415 A1* | 4/2011 | Ignon .................... A61B 17/54 604/22 |
| 2012/0321368 A1* | 12/2012 | Lim ...................... A45D 34/04 401/118 |
| 2013/0243514 A1* | 9/2013 | Ballot .................... B05C 1/00 401/109 |

\* cited by examiner

ANTISEPTIC APPLICATOR

CROSS-REFERENCE TO RELATED APPLICATION

This application is a Continuation of U.S. application Ser. No. 12/826,139, filed Jun. 29, 2010, the disclosure of the prior application is hereby incorporated in its entirety by reference.

BACKGROUND

Field

The present disclosure relates to an antiseptic applicator and method of use thereof, and more particularly, to a pull-activated antiseptic applicator that requires the application of opposing forces to actuate release of a sealed solution, preferably an antimicrobial solution, from a self-contained reservoir toward a material arranged at a distal end of the applicator for receiving the solution.

Description of Related Art

Antiseptic applicators for the preparation of a patient prior to surgery, for example, are known and common in the prior art. Conventional applicators rely on various means of actuation to release a self-contained reservoir of antimicrobial solution for sterilization of the patient's skin. For example, a number of applicators are designed with a puncturing means. These applicators typically include a head with a spike, for example, and a sealed container or cartridge. A push or screw motion is employed to axially translate the head toward the sealed container so that the spike may pierce the sealed container and effectuate the release of the solution contained therein. Some examples of applicators using a puncturing means include U.S. Pat. Nos. 4,415,288; 4,498,796; 5,769,552; 6,488,665; and 7,201,525; and U.S. Pat. Pub. No. 2006/0039742.

Other conventional applicators rely on breaking an internally situated frangible container or ampoule through the application of a one-way directional force or a localized application of pressure. The directional force is typically applied longitudinally to one end of the ampoule by a pushing motion designed to force the ampoule to break under a compressive stress, sometimes at a predetermined area of stress concentration. Alternatively, a pressure may be applied to a localized section of the ampoule through a squeezing motion designed to crush a section of the frangible ampoule in order to release the antimicrobial solution contained therein. Some examples of applicators using frangible ampoules in the manner discussed above include U.S. Pat. Nos. 3,757,782; 5,288,159; 5,308,180; 5,435,660; 5,445,462; 5,658,084; 5,772,346; 5,791,801; 5,927,884; 6,371,675; and 6,916,133.

Conventional antiseptic applicators, as described above, require special packaging and/or handling during shipping and prior to use. For example, with the puncture type applicators, preventive measures are required to prevent an inadvertent push against either end of the device that may result in the puncturing of the sealed container and the premature discharge of the solution. Similarly, the use of frangible ampoules requires special care to avoid breaking as a result of inadvertent pressure or dropping during shipping or prior to use. There exists a need in the field for a novel antiseptic applicator that avoids the complications associated with conventional applicators, especially an applicator that will reduce the safeguards currently required to prevent the loss of valuable inventory, for example.

SUMMARY

In accordance with aspects of the present invention, an applicator assembly includes a body having a proximal and a distal end, a container slidably coupled to the body, a valve cap, wherein the valve cap is coupled to the container, and an application member attached to the distal end, wherein an interior of the container is placed in fluid communication with the application member by way of a fluid conduit that is only accessible when one of the body and the container are axially translated in an opposite direction away from each other.

In accordance with another aspect of the present invention, the applicator assembly may further include an end cap having a female receptacle configured to mate with an extension portion of the valve cap to control the axial translation of the body and the container relative to one anther.

In accordance with another aspect of the present invention, the applicator assembly may include a closure mechanism that prevents communication between the interior of the container and the application member until the body and the container are axially translated in an opposite direction from each other.

In accordance with yet another aspect of the present invention, the applicator assembly, an applicator assembly may include a body having a proximal end and a distal end, a container slidably coupled to the body, a valve cap coupled to the container, an application member attached to the distal end, and means for providing fluid communication from an interior of the container to the application member when one of the body and the container are axially translated in an opposite direction away from each other.

It will become readily apparent to those skilled in the art from the following detailed description, wherein it is shown and described only exemplary configurations of a an applicator assembly. As will be realized, the invention includes other and different aspects of an applicator and assembly and the various details presented throughout this disclosure are capable of modification in various other respects, all without departing from the spirit and scope of the invention. Accordingly, the drawings and the detailed description are to be regarded as illustrative in nature and not as restrictive.

DETAILED DESCRIPTION

Various aspects of an antiseptic applicator may be illustrated by describing components that are coupled, attached, and/or joined together. As used herein, the terms "coupled", "attached", and/or "joined" are used to indicate either a direct connection between two components or, where appropriate, an indirect connection to one another through intervening or intermediate components. In contrast, when a component is referred to as being "directly coupled", "directly attached", and/or "directly joined" to another component, there are no intervening elements present.

Relative terms such as "lower" or "bottom" and "upper" or "top" may be used herein to describe one element's relationship to another element illustrated in the drawings. It will be understood that relative terms are intended to encompass different orientations of an antiseptic applicator in addition to the orientation depicted in the drawings. By way of example, if an antiseptic applicator in the drawings is turned over, elements described as being on the "bottom" side of the other elements would then be oriented on the "top" side of the other elements. The term "bottom" can therefore encompass both an orientation of "bottom" and "top" depending on the particular orientation of the apparatus.

Various aspects of an antiseptic applicator may be illustrated with reference to one or more exemplary embodiments. As used herein, the term "exemplary" means "serving as an example, instance, or illustration," and should not necessarily be construed as preferred or advantageous over other embodiments of an antiseptic applicator disclosed herein.

Figure 1:
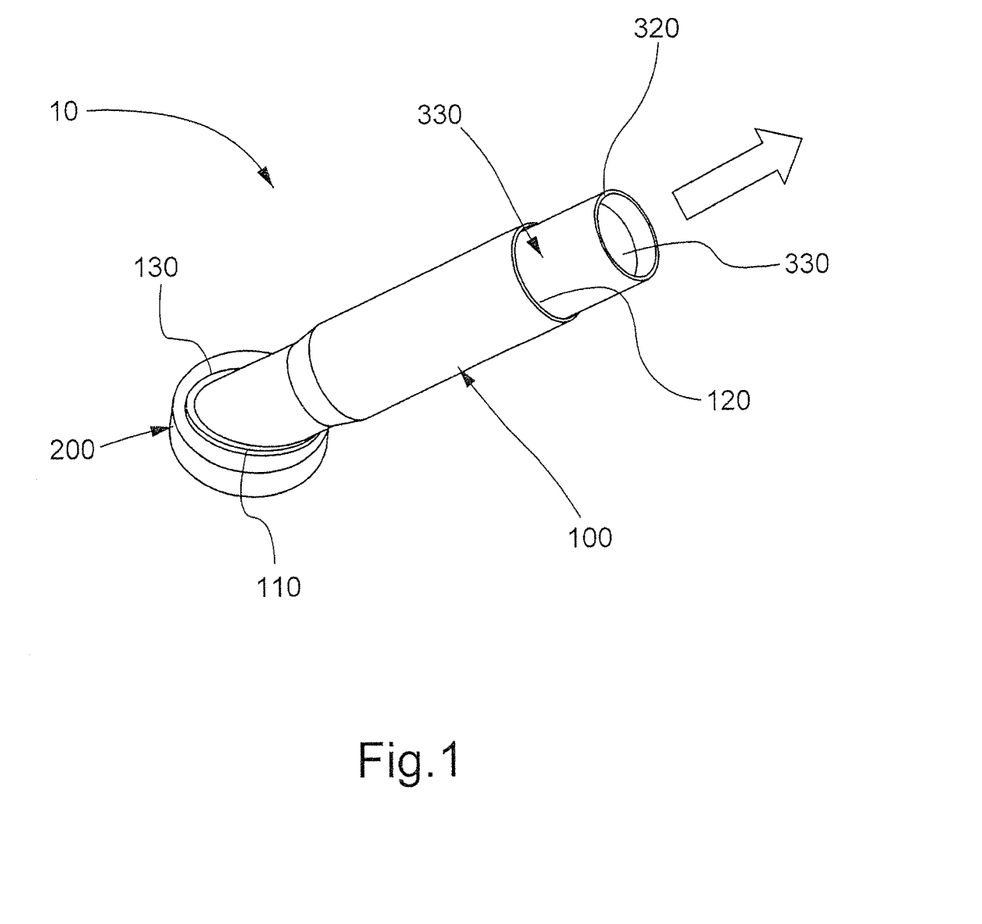
FIG. 1 is a perspective view of an antiseptic applicator, in accordance with certain aspects of the present invention.
Figure 2:
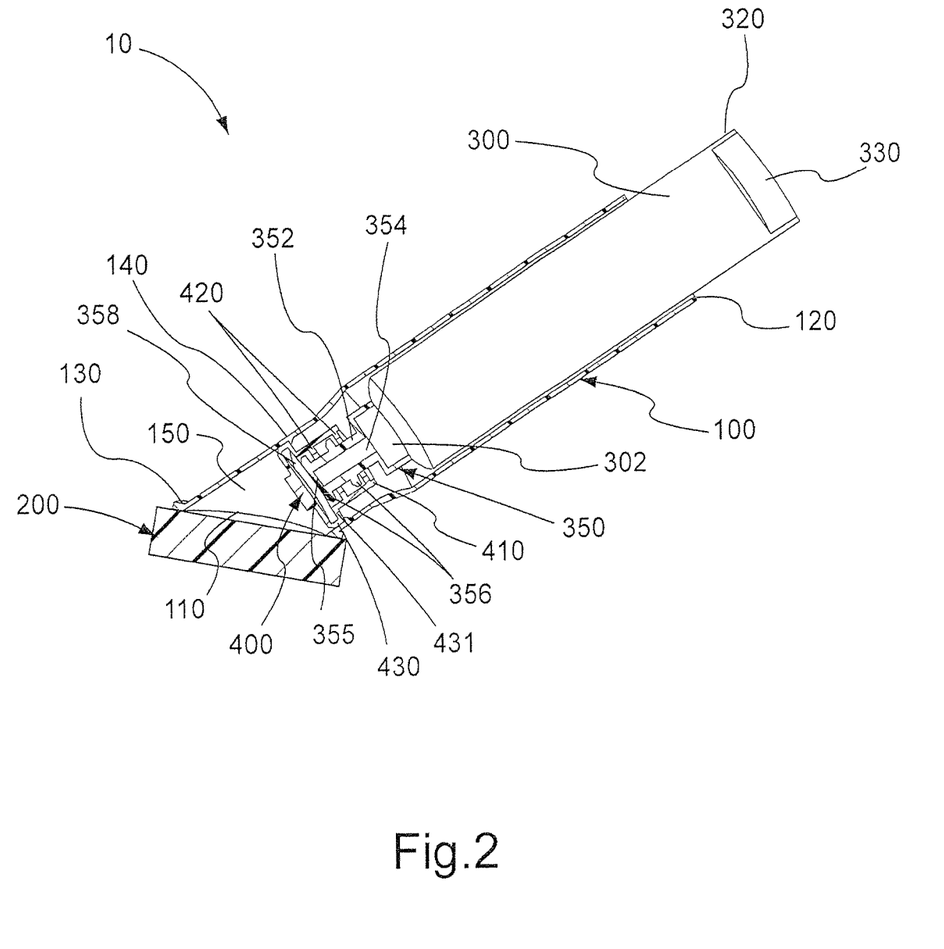
FIG. 2 is a side cutaway view of an antiseptic applicator, in accordance with certain aspects of the present invention.

The antiseptic applicator may be compact and ergonomically designed. As shown in FIGS. 1 and 2, an antiseptic applicator 10 may comprise a substantially hollow body 100, which may be cylindrical in shape, an application member 200 mounted to a distal end 110 of the body 100, and a solution container 300 slidably received by a proximal end 120 of the body 100. The solution container 300 may be cylindrical in shape to position concentrically into the body 100 with a proximal end 320 extending beyond the proximal end 120 of the body 100. The solution container 300 may be formed with a grasping mechanism 330, which may be a recessed area in the proximal end 320. The grasping mechanism 330 provides a hand-hold, for example, to enhance the ability of a user to pull the solution container 300 in one direction with one hand, while holding and/or pulling the body 100 with the other hand, in order to translate the solution container 300 in an axial direction away from the distal end 110 of the body 100.

The application member 200 may be formed from a foam sponge material, for example, or any suitable material that allows the controlled application of the contained solution from the solution container 300 to a surface external to the applicator 10. The material chosen may be porous with a particular soak rate, for example, or may be provided with structural features, including slits or apertures, to direct and control the flow rate of the solution through the application member 200. The body 100 may be configured to have a mounting flange 130 at the distal end 110. The mounting flange 130 provides a surface for affixing the application member 200 to the body 100.

The solution container 300 is preferably a self-contained structure, formed of a suitable material, such as a high-density polyethylene plastic, that is flexible, yet resistant to deformation and chemical leeching. The container 300 may be filled with various liquids such as antiseptics or medicaments, chemical compositions, cleansing agents, cosmetics, or the like, and preferably an antimicrobial liquid or gel composition, such as a chlorhexadine gluconate solution, for antiseptic application to a patient prior to surgery. The container 300 is designed to withstand various heat and chemical sterilization techniques, which may be performed sequentially with a solution filling process, in accordance with techniques that are well known in the art.

As shown in FIG. 2, the container 300 may be formed with a neck portion 302. A valve cap 350 may be press fit onto the neck portion 302, for example, or designed for a threaded connection to external threads provided on the neck portion. The valve cap 350 is formed with an extension portion 352 for mating with a female receptacle 410 of an end cap 400. For example, at least one retaining annulet 356 may be provided on an exterior surface of the extension portion 352, and at least one retaining lip 420 may be provided on an interior surface of the female receptacle 410. The retaining annulets 356 may be configured with beveled edges on a distal side to facilitate the insertion of the extension portion 352 into the female receptacle 410 during assembly. The proximal side of the annulets 356 may be formed to cooperate with the lips 420 to limit the axial movement of the container 300 in relation to the body 100 and to prevent the separation of the container 300 from the body 100 once joined in a final assembled position. The extension portion 352 may be formed with an interior fluid passage 354 that provides communication between an opening 355 in the valve cap 350 and the interior of the container 300 containing the solution.

The end cap 400 may be integrally formed with the body 100 or, as shown in FIG. 2, a retention lip 140 may be formed on an inner surface of the body 100 towards the distal end 110. The retention lip 140 cooperates with an end flange 430 of the end cap 400 to prevent axial displacement of the end cap 400 toward the proximal end 120 of the body 100 when the end flange 430 abuts against the retention lip 140. Thus, during assembly, for example, the end cap 400 may be inserted through the distal end 110 of the body 100 with the female receptacle 410 opening toward the proximal end 120 of the body 100. The body 100, with the end cap 400 positioned therein, may be mounted onto the solution filled container 300 by mating the female receptacle 410 onto the extension portion 352 of the valve cap 350, the valve cap 350 being fixedly attached to the container 300. In this manner, a compressive force is applied that is large enough to ensure that the retaining annulets 356 snap through the retaining lips 420 when the receptacle 410 is mounted onto the extension 352.

As shown in FIG. 2, with the container 300 concentrically mounted in the body 100, as described above, and the application member 200 mounted to close off the distal end 110 of the body 100, a fluid chamber 150 may be formed in the distal end of the body 100 between the application member 200 and the end cap 400. A fluid metering device, such as a pledget, for example, may be optionally provided in the fluid chamber 150 to further control and/or direct the flow of solution from the container 300 when the assembly 10 is in use.

Figure 3:
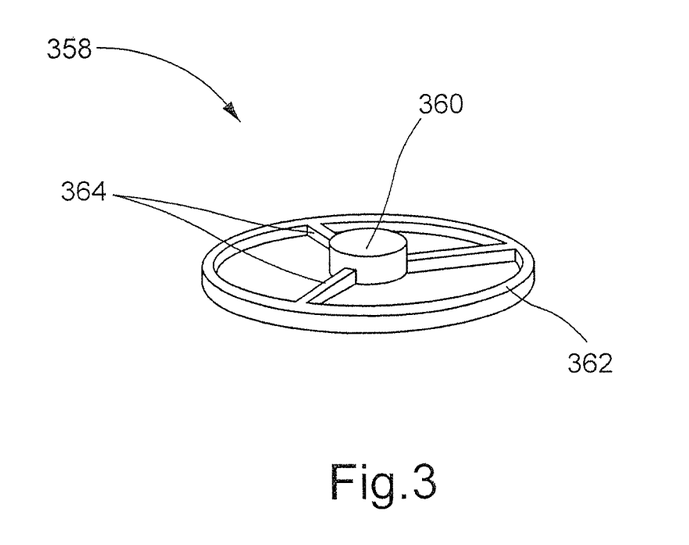
FIG. 3 is a perspective view of an exemplary leak proof mechanism, in accordance with certain aspects of the present invention.

A closure mechanism 358 may be provided with the end cap 400 to prevent solution from leaking into the fluid chamber 150 unless the applicator is intentionally activated for use. For example, as shown in FIG. 3, the closure mechanism 358 may comprise a centrally located closure mechanism 360, such as a plug, connected to a peripheral retaining ring 362 by support struts 364. As shown in FIG. 2, the closure mechanism 358 may be retained in a hollow, inner portion of the end flange 430. The peripheral retaining ring 362 is configured to have an external radius greater than a radial dimension of the receptacle 410. As such, the closure mechanism 358 is prevented from any significant axial displacement in the direction of the proximal end 110 due to the retaining ring 362 engaging a step seat 431 formed by the radial extension of a proximal surface of the end flange 430.

The closure mechanism 360 of the closure mechanism 358 slidably engages the valve opening 355 in the extension portion 352. In a storage position, or as initially assembled, for example, the closure mechanism 360 may be fully inserted into the valve opening 355, effectively preventing any discharge of fluid from the container 300. Preferably, the closure mechanism 360 has an outer radial dimension equal to or slightly larger than the inner radial dimension of the valve opening 355. In this manner, a level of applied force is necessary to engage or disengage the closure mechanism 360 with the valve opening 355.

To activate the applicator 10 and release the solution from the container 300, a user may grasp the body 100 with one hand and the container 300 with the other hand, for example by way of the grasping mechanism 330, and pull one or both of the body 100 and the container 300 in axially opposing directions away from each other. The application of opposing force translates the extension 352 from a forwardly disposed position toward the proximal end 120 of the body 100. As the extension 352 translates proximally in relation to the body 100, the peripheral retaining ring 362 of closure mechanism 358 abuts against the step seat 431. Continued applied force by the container 300 axially translating in a proximal direction pulls on the closure mechanism 360 that is press fit into the valve opening 355, straining the closure mechanism 358 under the pressure. When the applied force overcomes the resistance of the press fit bond, for example, the closure mechanism 360 releases from the valve opening 355, which may be accompanied by an audible and tactile snap due to the sudden release of pressure and the natural rebound of the closure mechanism 358. The closure mechanism 360 is thus released from the valve opening 355, placing the inside of the container 300 in fluid communication with the application member 200 via the fluid chamber 150 and the fluid channel 354, for example. According to another aspect of the invention, the inner portion of the end flange 430 may provide fluid communication directly to the application member 200 without the intervening fluid chamber 150.

With the plug 360 removed from the valve opening 355, positioning the applicator 10 with the application member 200 situated below the container 300 allows the solution to drain from the container 300 under its own weight. Further axial translation of the container 300 in a proximal direction relative to the body 100 increases the gap between the plug 360 and the valve opening 355, which may increase the flow of the solution from the container 300. The solution flows from the container 300, through the fluid passage 354 and the valve opening 355, and into the fluid chamber 150. The solution may soak into, or otherwise flow through, the application material 200 at a specified volume and rate. The fluid chamber 150 may serve to accumulate and distribute the solution evenly over substantially the entire area of the application material 200. Once the application material 200 is engorged, for example, the solution may then be applied to a patient by wiping the distal surface of the application material 200 against the skin.

Figure 4:
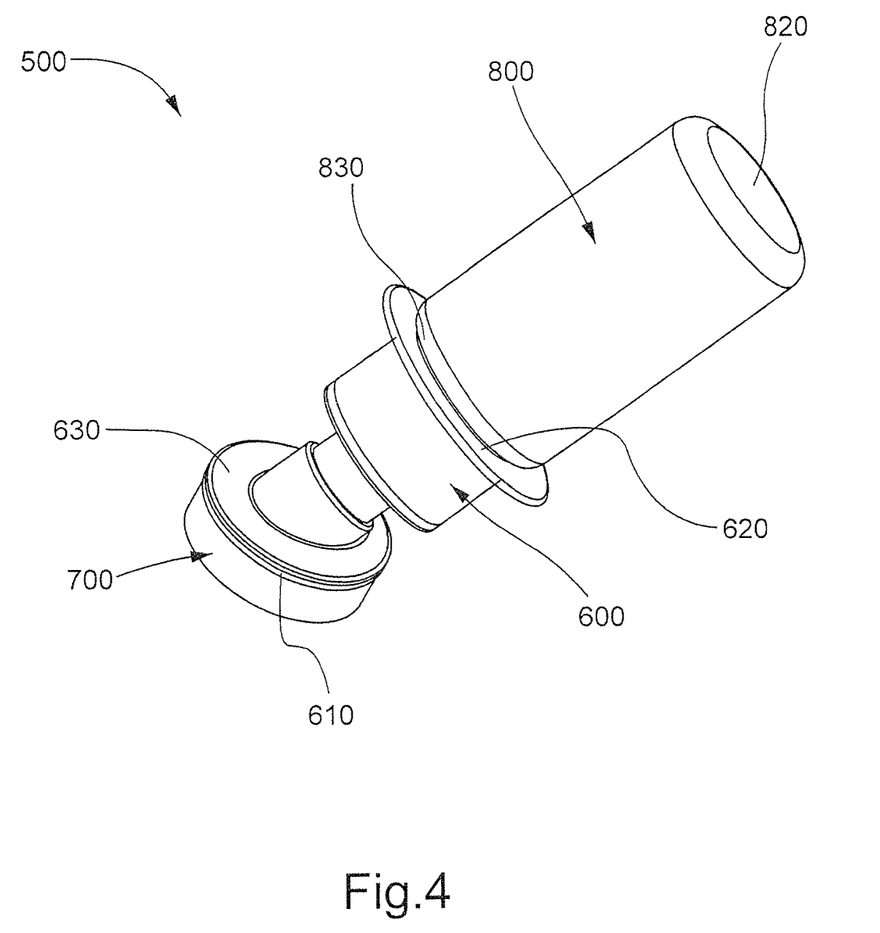
FIG. 4 is a perspective view of an antiseptic applicator, in accordance with certain aspects of the present invention.
Figure 5:
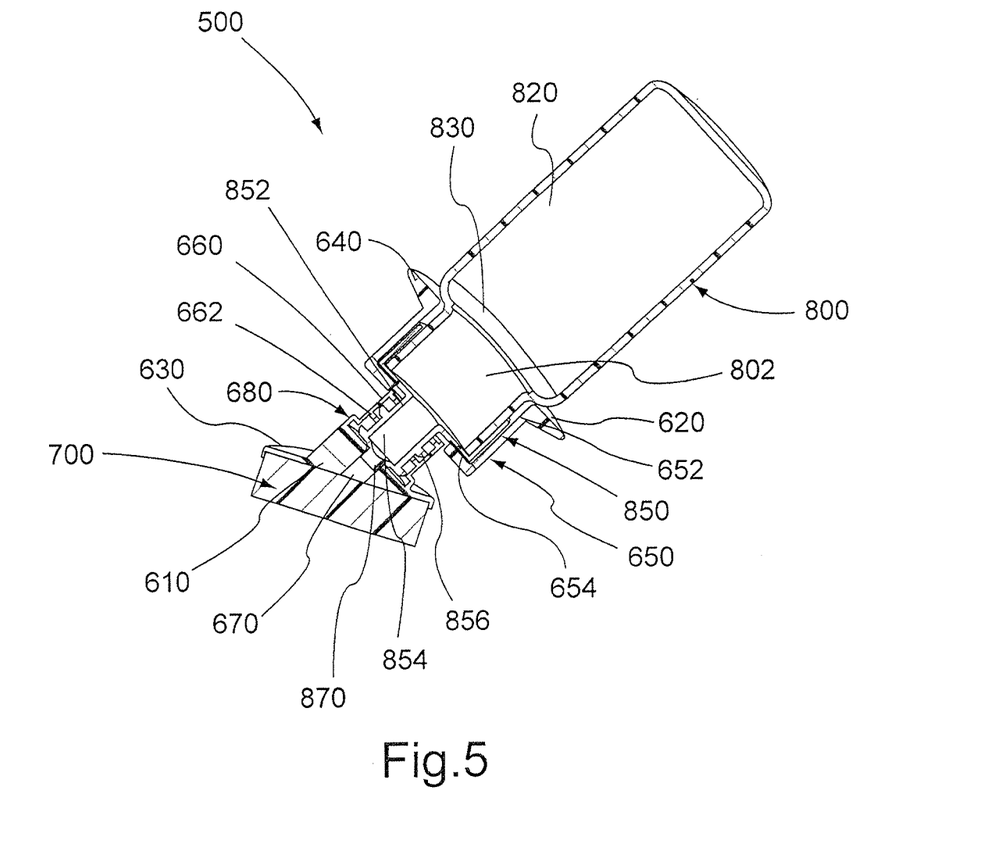
FIG. 5 is a side cutaway view of an antiseptic applicator, in accordance with certain aspects of the present invention.

FIGS. 4 and 5 illustrate an antiseptic applicator 500 in accordance with other aspects of the present invention. The antiseptic applicator 500 may have a body 600, an application member 700 mounted to a distal end 610 of the body 600, and a solution container 800 slidably received by a proximal end 620 of the body 600.

The application member 700 may be formed from a foam sponge material, for example, or any suitable material that allows the controlled application of the contained solution from the solution container 800 to a surface external to the applicator 500. The material chosen may be porous with a particular soak rate, for example, or may be provided with structural features, such as slits or apertures, to direct and control the flow rate of the solution through the application member 700. The body 600 may be configured to have a mounting flange 630 at the distal end 610. The mounting flange 630 provides a surface for affixing the application member 700 to the body 600.

The solution container 800 is preferably a self-contained structure, formed of a material, such as a high-density polyethylene plastic that is flexible, yet resistant to deformation and chemical leeching. The container 800 may be filled with a solution, preferably an antimicrobial liquid or gel composition, for antiseptic application to a patient prior to surgery. The container 800 is designed to withstand various heat and chemical sterilization techniques, which may be performed sequentially with a solution filling process, in accordance with techniques that are well known in the art.

As shown in FIG. 5, the body includes an annular flange 640 at a proximal end 620 and the mounting flange 630 at the distal end 610. The body is open at the proximal end 620 and includes a receiving bore 650 for receiving and supporting the container 800. The receiving bore 650 may be a circular recess, for example, having a side wall 652 that connects the annular flange 640 to a lower support surface 654.

The container 800 may be generally cylindrical in shape, for example, and may be formed with a cylindrical neck portion 802 extending from a wider container portion 820. A smooth step seat 830 is formed on a peripheral surface of the container 800 where the cylindrical neck portion 802, having a predetermined insertion diameter, concentrically transitions to the wider container portion 820, having a larger diameter than the insertion diameter.

Figure 6:
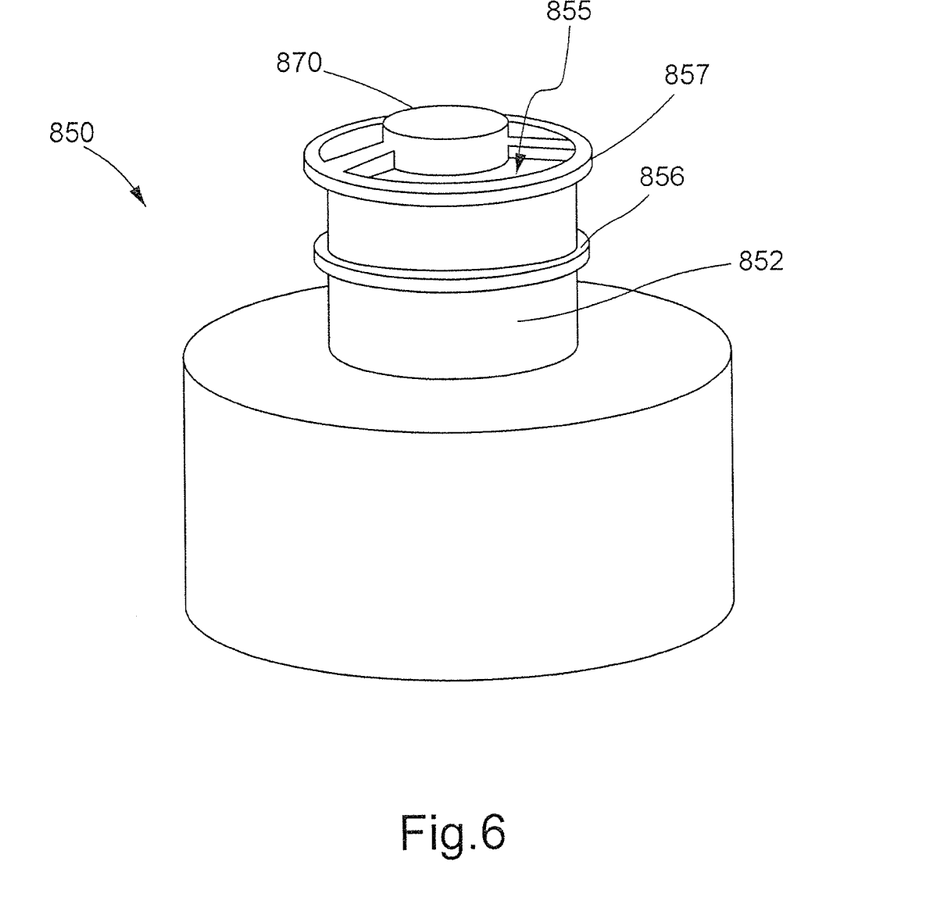
FIG. 6 is a perspective view of an exemplary valve cap, in accordance with certain aspects of the present invention.

A valve cap 850 may be press fit onto the neck portion 802, for example, or designed for a threaded connection to external threads provided on the neck portion 802. As shown in FIGS. 5 and 6, the valve cap 850 is formed with an extension portion 852 for mating with a female receptacle 660 of the body 600. The female receptacle 660 may be cylindrical in shape and extend from the lower support surface 654 toward the distal end 610. For example, at least one retaining annulet 856 may be provided on an exterior surface of the extension portion 852 and at least one valve retaining lip 662 may be provided on an interior surface of the female receptacle 660. The retaining annulets 856 may be configured with a beveled edge on a distal side to facilitate the insertion of the extension portion 852 into the female receptacle 660 during assembly. The proximal side of the annulets 856 may be formed to cooperate with the lips 662 to limit the axial movement of the container 800 in relation to the body 600 and to prevent the separation of the container 800 from the body 600 once joined in a final assembled position. The extension portion 852 is formed with an interior fluid passage 854 that provides communication between an opening 855 in the valve cap 850 and the interior of the container 800 containing the solution. A closure mechanism 870, such as a plug, is mounted to the valve cap 850 and cooperates with a distal fluid passage 670 in the body 600 to control fluid flow to the application member 700.

To assemble the applicator 500, for example, the receiving bore 650 slidably receives the neck portion 802 of the container 800 having the valve cap 850 fixedly attached thereto. The extension portion 852 of the valve cap 850 mates with the female receptacle 660 of the body 600. In this manner, a compressive force is applied that is large enough to ensure that the at least one retaining annulet 856 snaps through the at least one valve retaining lip 662.

As shown in FIG. 5, with the container 800 concentrically mounted in the body, as described above, and the application member 700 mounted to the distal end 610 of the body, the plug 870 is slidably received into the distal fluid passage 670. A fluid metering device, such as a pledget, for example, may be optionally provided in the distal fluid passage 670 to further control the flow of solution from the container 800 when the assembly 500 is activated. In a storage position, or as initially assembled, for example, the plug 870 may be fully inserted into the distal fluid passage 670, effectively preventing any discharge of fluid through the distal fluid passage 670. Preferably, the closure mechanism 870 has an outer radial dimension sufficient to plug the distal fluid passage, for example, equal to or slightly larger than the inner radial dimension of the distal fluid passage 670. In this manner, a certain level of force is necessary to engage or disengage the closure mechanism 870 with the distal fluid passage 670.

As shown in FIG. 5, another aspect in accordance with the present invention may be a snap seal mechanism 680. The snap seal mechanism 680 is formed so as to retain a distal retaining annulet 857 until a certain level of applied force causes deformation of the annulet 857. At a predetermined point of deformation, the annulet 857 will release from the snap seal mechanism 680, preferably accompanied by an audible and tactile snap due to the sudden release of pressure. The closure mechanism 870 may then be extracted from the distal fluid passage 670 by axial translation of the container 800, allowing the inside of the container 800 to be in fluid communication with the application member 700 by way of the distal fluid passage 670.

To activate the applicator 500 and release the solution from the container 800, a user may grasp the container 800 with one hand and preferably push against the annular flange 640 to force the body 600 and the container 800 to move in axially opposing directions away from each other. The application of opposing force translates the extension 852 from a forwardly disposed position toward the proximal end 620 of the body 600. As the extension 852 translates proximally in relation to the body 600, the snap seal mechanism 680 releases the distal annulet 857 with a snap, and the closure mechanism 870 releases from the fluid passage 670.

With the closure mechanism 870 removed from distal fluid passage 670, positioning the applicator 500 with the application member 700 situated below the container 800 allows the solution to drain from the container 800 under its own weight. Further axial translation of the container 800 in a proximal direction relative to the body 600 increases the gap between the closure mechanism 870 and the distal fluid passage 670, which may increase the flow of the solution from the container 800. The solution flows from the container 800, through the fluid passage 854 and the opening 855, and into the distal fluid passage 670. The solution may soak into, or otherwise flow through, the application material 700 at a specified volume and rate. The solution may be applied to a patient, for example, by wiping the application material 700 against the skin.

The previous description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but is to be accorded the full scope consistent with the language claims, wherein reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. An applicator assembly comprising:
a body having a proximal end, a distal end, and an interior surface;
a container having an outer surface, the container being slidably coupled to the body;
a valve cap having a proximal end and a distal end, wherein the valve cap is coupled to the container via the proximal end of the valve cap;
an application member attached to the distal end of the body; and
an end cap having an end flange and a female receptacle extending from the end flange,
wherein the end flange abuts the interior surface of the body,
wherein the entire distal end of the valve cap mates within the female receptacle,
wherein an interior of the container is placed in fluid communication with the application member by way of a fluid conduit that is only accessible when one of the body and the container are axially translated along the longitudinal axis in the opposite direction away from each other.

2. The applicator assembly of claim 1, wherein the valve cap further comprises an extension portion, and wherein the female receptacle is configured to mate with the extension portion to control the axial translation of the body and the container relative to one another.

3. The applicator assembly of claim 2, wherein the female receptacle comprises a retaining lip and the extension portion comprises a retaining annulet, and wherein the retaining lip cooperates with the retaining annulet to prevent separation of the body and the container.

4. The applicator assembly of claim 2, further comprising a closure member mounted in the female receptacle, wherein the closure member prevents communication between the interior of the container and the application member until the body and the container are axially translated in an opposite direction from each other.

5. The applicator assembly of claim 4, wherein the valve cap comprises a fluid passage, and wherein the closure member comprises a centrally located portion that slidably engages a distal opening of the fluid passage.

6. The applicator assembly of claim 5, wherein the closure member further comprises a peripheral retaining ring connected to the centrally located portion by support struts.

7. The applicator assembly of claim 6, wherein the peripheral retaining ring is situated in the end flange and applies resistance to the axial translation of the body and container relative to one another.

8. The applicator assembly of claim 1, wherein the fluid conduit is provided in the end flange and provides fluid communication directly to the application member.

9. The applicator assembly of claim 1, further comprising a solution provided in the container.

10. The applicator assembly of claim 9, wherein the fluid conduit for receiving the solution from the container is formed at the distal end of the body between the valve cap and the application member.

11. The applicator assembly of claim 1, wherein the body further comprises a mounting flange having a mounting surface, and the application member is attached to the mounting surface.

12. The applicator assembly of claim 1, wherein the fluid conduit is a fluid chamber formed in the distal end of the body.

13. An applicator assembly comprising:
a body having a proximal end and a distal end;
a container having a neck portion and an outer surface, the container being slidably coupled to the body;
a valve cap comprising:
 a base portion disposed between the body and the neck portion of the container; and
 an extension portion extending axially from the base portion, wherein the valve cap is coupled to the container;
a closure member mounted to the extension portion of the valve cap; and
an application member attached to the distal end,
wherein the body comprises a receiving bore for slidably receiving the neck portion,
wherein an interior of the container is placed in fluid communication with the application member by way of a fluid conduit that is only accessible when one of the body and the container are axially translated along the longitudinal axis in the opposite direction away from each other.

14. The applicator assembly of claim 13, wherein the body further comprises a receptacle portion configured to mate with the extension portion to control the axial translation of the body and the container relative to one another.

15. The applicator assembly of claim 14, wherein the receptacle portion comprises a retaining lip and the extension portion comprises a retaining annulet, and wherein the retaining lip cooperates with the retaining annulet to prevent separation of the body and the container.

16. The applicator assembly of claim 13, wherein the fluid conduit is provided in the distal end of the body.

17. The applicator assembly of claim 13, wherein the closure member comprises a centrally located portion that slidably engages a proximal opening of the fluid conduit and prevents communication between the interior of the container and the application member until the body and the container are axially translated in an opposite direction away from each other.

18. The applicator assembly of claim 13, wherein the body further comprises a snap seal mechanism and the extension portion further comprises a distal retaining annulet, and wherein the snap seal mechanism cooperates with the distal retaining annulet to provide resistance to the axial translation of the body and container relative to one another.

19. The applicator assembly of claim 13, wherein the body further comprises a distal flange provided about a proximal rim of the receiving bore.

20. The applicator assembly of claim 19, wherein the container further comprises a wider container portion having a larger diameter than an insertion diameter of the neck portion, and wherein a smooth step seat is formed on a peripheral surface of the container where the neck portion concentrically transitions to the wider container portion.

* * * * *